(12) United States Patent
Kase et al.

(10) Patent No.: US 6,476,259 B2
(45) Date of Patent: Nov. 5, 2002

(54) CATALYSTS FOR METHACRYLIC ACID PRODUCTION AND PROCESS FOR PRODUCING METHACRYLIC ACID

(75) Inventors: Yuichi Kase, Himeji (JP); Hideo Onodera, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/983,085

(22) Filed: Oct. 23, 2001

(65) Prior Publication Data

US 2002/0052529 A1 May 2, 2002

Related U.S. Application Data

(62) Division of application No. 09/557,295, filed on Apr. 25, 2000.

(30) Foreign Application Priority Data

Apr. 27, 1999 (JP) ............................................ 11/119171

(51) Int. Cl.[7] ........................ C07C 51/16; C07C 51/235; B01J 23/00
(52) U.S. Cl. ........................ 562/532; 562/534; 562/535; 562/599; 562/208; 562/209; 562/211; 562/300
(58) Field of Search ............................... 562/532, 534, 562/535, 599; 502/208, 209, 211, 300

(56) References Cited

U.S. PATENT DOCUMENTS

| | | | | |
|---|---|---|---|---|
| 4,564,703 A | * | 1/1986 | Yamamoto et al. | |
| 5,206,431 A | * | 4/1993 | Hashiba et al. | |

FOREIGN PATENT DOCUMENTS

JP 09-299803 * 11/1997

OTHER PUBLICATIONS

English Translation of JP 09–299803, by Takako et al.*

* cited by examiner

*Primary Examiner*—Sreeni Padmanabhan
*Assistant Examiner*—Farhad Forohar
(74) *Attorney, Agent, or Firm*—Sherman & Shalloway

(57) ABSTRACT

Improved catalyst for use in production of methacrylic acid by vapor phase oxidation reaction and/or vapor phase oxidative dehydrogenation reaction of at least one compound selected from methacrolein, isobutylaldehyde and isobutyric acid is provided. This improved catalyst is a composition composed of (A) complex oxide containing as essential components molybdenum and phosphorus, which is per se known as a catalyst for the above reaction(s), and (B) complex oxide containing as essential components cerium and zirconium. When this improved catalyst is used, the operation for producing methacrylic acid can be stably continued over prolonged period.

3 Claims, No Drawings

CATALYSTS FOR METHACRYLIC ACID PRODUCTION AND PROCESS FOR PRODUCING METHACRYLIC ACID

This application is a divisional of prior application Ser. No. 09/557,295 filed Apr. 25, 2000.

TECHNICAL FIELD TO WHICH THE INVENTION BELONGS

This invention relates to catalysts for methacrylic acid production and also to a process for producing methacrylic acid. More particularly the invention relates to improved catalysts for producing methacrylic acid at high yield stably over prolonged period, by vapor phase oxidation and/or vapor phase oxidative dehydrogenation of at least one compound selected from the group consisting of methacrolein, isobutylaldehyde and isobutyric acid; and to a process for producing methacrylic acid using the improved catalyst.

CONVENTIONAL TECHNOLOGY

Various improved catalysts have been proposed for high efficiency production of methacrylic acid by vapor phase catalytic oxidation and/or vapor phase oxidative dehydrogenation reaction of methacrolein, isobutylaldehyde or isobutyric acid. For example, JP Kokai Sho 55 (1980)-2619A1 has disclosed a catalyst which contains as the essential components Mo, V, P and at least one of K, Rb, Cs and Tl; JP Kokai Sho 60 (1985)-239439 A1 has disclosed a catalyst which contains as the essential components Mo; V; P; at least one of K, Rb, Cs and Ti; at least one of Sc, Y, La, Ce, Pr, Nd, Pu and Sm; and at least one of Cu, As, Sb, Co, Zr, Bi, Ti, Te and Ag. Inferring from the methods of their preparation, those known catalysts whose chief components are molybdenum and phosphorus are basically considered to be phosphomolybdic acid or salts thereof (e.g., ammonium salts or alkali metal salts) and structurally they are mixtures of heteropolyacids or their analogues.

Those catalysts, however, are still open to further improvements in respect of methacrylic acid yield and their life. Because heteropolyacids have low heat resistance, those catalysts show decomposition of the heteropolyacid structure when used for prolonged period. Therefore, in order to obtain a catalyst for methacrylic acid production which exhibits stable performance over a prolonged period, it is necessary either to increase stability of heteropolyacid or to find a highly active heteropolyacid which is useful as the catalyst also at relatively low temperatures.

JP Kokai Sho 61 (1986)-5043 A1 has disclosed a catalyst whose essential components comprise; Mo; V; P; Ce; at least one of K, Rb, Cs and Tl; and at least one of Cu, As, Sb, Co, Zr, Bi, Ni, Cr, Mn and Zn. However, such a catalyst composed of conventional components to which cerium component is simply added is yet insufficient as to improvement in the catalyst life because cerium oxide aggregates with time.

On the other hand, various proposals have been also made as to complex oxides whose essential components are cerium and zirconium. Most of these complex oxides are known as additive components to waste gas-purging catalysts, but it is entirely unknown that such complex oxides whose essential components are cerium and zirconium exhibit effective catalytic activity in methacrylic acid-forming reaction comprising vapor phase oxidation and/or vapor phase oxidative dehydrogenation of methacrolein, isobutylaldehyde or isobutyric acid, when used in combination with heteropolyacid catalyst.

OBJECTS OF THE INVENTION

One of the objects of the present invention is to provide catalysts useful in production of methacrylic acid at high yield.

A further object of the present invention is to provide catalysts for methacrylic acid production, which have long catalyst life and enable stable operation over prolonged period.

Still another object of the present invention is to provide catalysts for methacrylic acid production which enable stable operation over prolonged period, even under heavy load operation aiming at high productivity.

An additional object of the present invention is to provide a process for producing methacrylic acid at high yield and stably over prolonged period, using the above catalysts.

MEANS TO SOLVE THE PROBLEMS

We have discovered that a composition in which a catalyst known as that for methacrylic acid production, containing molybdenum and phosphorus as the essential components, is combined with a complex oxide whose essential components are cerium and zirconium exhibits high activity in the intended reaction and excellent stability; and that the use of such a composition as a catalyst in said reaction accomplishes the above objects.

Thus, according to the invention, as a catalyst for producing methacrylic acid through oxidation and/or oxidative dehydrogenation of at least one compound selected from the group consisting of methacrolein, isobutylaldehyde and isobutyric acid with molecular oxygen or a molecular oxygen-containing gas at vapor phase, a complex oxide composition characterized by comprising (A) a complex oxide containing as essential components molybdenum and phosphorus, which is known per se as a catalyst for said vapor phase catalytic oxidation and/or vapor phase oxidative dehydrogenation reaction, and (B) a complex oxide containing cerium and zirconium as the essential components, is provided.

According to the present invention, there is also provided, as a catalyst for producing methacrylic acid through oxidation and/or oxidative dehydrogenation of at least one compound selected from the group consisting of methacrolein, isobutylaldehyde and isobutyric acid with molecular oxygen or a molecular oxygen-containing gas at vapor phase, a complex oxide composition which is characterized by having a composition expressed by the following general formula (3):

$$P_aMo_bCe_cZr_dA_eB_fC_gD_hE_iG_jO_x \quad (3)$$

(wherein P is phosphorus; Mo is molybdenum; Ce is cerium; Zr is zirconium; A is at least an element selected from the group consisting of arsenic, antimony, germanium, bismuth and selenium; B is at least an element selected from the group consisting of copper, silver, iron, cobalt, nickel, lead, manganese, chromium, tin, zinc, palladium, rhodium and tellurium; C is at least an element selected from the group consisting of tungsten, vanadium and niobium; D is at least an element selected from the group consisting of alkali metals and alkaline earth metals; E is at least an element selected from the group consisting of titanium, silicon and aluminium; G is at least an element selected from the group consisting of lanthanoide series elements except cerium; yttrium and indium; and O is oxygen; a, b, c, d, e, f, g, h, i, j and x denote the atomic ratios of P, Mo, Ce, Zr, A, B, C, D, E, G and O, respectively; and where b is 12, a is 0.5–4, c is 0.01–12, d is 0.01–16, e is 0.01–3, f is 0.01–5, g is 0.01–5, h is 0.01–6, i is 0.01–10 and j is 0.001–2, and x is a numerical value determined by degree of oxidation of each of the elements)

and the cerium and zirconium therein forming a complex oxide.

According to the invention, furthermore, there is provided a process for producing methacrylic acid through vapor phase oxidation and/or oxidative dehydrogenation of at least one compound selected from the group consisting of methacrolein, isobutylaldehyde and isobutyric acid with molecular oxygen or a molecular oxygen-containing gas, in the presence of a catalyst, the process being characterized in that it uses the above-defined complex oxide composition as the catalyst.

EMBODIMENTS OF THE INVENTION

Catalyst (I) for methacrylic acid production according to the invention is a complex oxide composition which is characterized by comprising (A) a complex oxide containing as essential components molybdenum and phosphorus, which is known per se as a catalyst for producing methacrylic acid through said vapor phase catalytic oxida- tion and/or vapor phase oxidative dehydrogenation reaction of methacrolein, isobutylaldehyde or isobutyric acid, and (B) a complex oxide containing cerium and zirconium as the essential components.

Catalyst (II) for methacrylic acid production according to another embodiment of the present invention is a complex oxide composition which is characterized by having the composition as expressed by above general formula (3), in which cerium and zirconium form a complex oxide.

First, the Catalyst (I) shall be explained. The component (A) corresponds to a catalyst containing molybdenum and phosphorus as the essential components, which is known as a catalyst for methacrylic acid production by vapor phase oxidation and/or vapor phase oxidative dehydrogenation reaction of methacrolein, isobutylaldehyde or isobutyric acid. While any of known catalysts containing molybdenum and phosphorus as the essential components can be used as the component (A), those preferred are expressed by the following general formula (1):

$P_aMo_bA_cB_dC_eD_fE_gO_x$           (1)

(wherein P is phosphorus; Mo is molybdenum; A is at least an element selected from the group consisting of arsenic, antimony, germanium, bismuth and selenium; B is at least an element selected from the group consisting of copper, silver, iron, cobalt, nickel lead, manganese, chromium, tin, zinc, palladium, rhodium and tellurium; C is at least an element selected from the group consisting of tungsten, vanadium and niobium; D is at least an element selected from the group consisting of alkali metals and alkaline earth metals; E is at least an element selected from the group consisting of titanium, silicon and aluminium; and O is oxygen; a, b, c, d, e, f, g and x denote the atomic ratios of P, Mo, A, B, C, D, E and O, respectively; and where b is 12, a is 0.5–4, preferably 0.5–3, c is 0.01–3, preferably 0.01–2, d is 0.01–5, preferably 0.01–3, e is 0.01–5, preferably 0.01–3, f is 0.01–6, preferably 0.01–3 and g is 0.01–10, preferably 0.01–5; and x is determined by degree of oxida- tion of each of the elements).

Method of preparing those catalysts is subject to no critical limitation, and the catalysts can be prepared by any known method. Kinds of the compounds containing the catalytic elements, which serve as the starting materials, are not critical but any oxides containing the catalytic elements or compounds capable of forming such oxides upon being calcined can be used. As the compounds which form oxides upon calcining, for example, hydroxides, metallic acids, nitrates, carbonates, ammonium salts, acetates and formates may be named. Compounds containing more than one of the elements are also useful. For instance, specific examples of molybdenum-containing compounds include molybdenum trioxide, ammonium paramolyb-date, molybdic acid, phosphomolybdic acid and phosphovanado-molybdic acid.

Normally each prescribed amount of those starting compounds containing the component elements are, for example, suitably dissolved in an aqueous medium, heated under stirring, evaporated to dry solid and optionally pulverized to provide the intended component (A).

As the component (B), any complex oxide which contains cerium and zirconium as the essential components can be used. In particular, complex oxides which are expressed by the following general formula (2):

$Ce_lZr_mF_nO_y$           (2)

(wherein Ce is cerium; Zr is zirconium; F is at least an element selected from the group consisting of lanthanoide series elements except cerium; yttrium, cobalt, nickel copper, indium, tin, chromium and germanium; and O is oxygen; l, m, n and y denote the atomic ratios of Ce, Zr, F and O, respectively, l and m being optional numbers not including 0, n being a number satisfying the relationship $0 \leq n/(l+m) < 0.1$, and y being a number determined by degree of oxidation of each of the elements)

are conveniently used. More specifically, when l=1, $0.01 \leq m \leq 99$, $0 \leq n < 10$, preferably $0.05 \leq m \leq 19$ and $0 \leq n \leq 2$.

Method of preparing complex oxides containing cerium and zirconium as the essential components is subject to no critical limitation, and they can be prepared by any known method. Kinds of the compounds containing the named elements, which serve as the starting materials, are not critical but any oxides containing the named elements or compounds capable of forming such oxides upon being calcined can be used. As the compounds which form oxides by calcining, for example, hydroxides, metallic acids, nitrates, carbonates, ammonium salts, acetates and formates may be named. For example, as a specific example of cerium-containing compound, cerium nitrate may be named.

Of the complex oxides expressed by the general formula (2), those in which cerium oxide and zirconium oxide are at least partially form a solid solution are conveniently used. In particular, those in which the molar ratio of $CeO_2/ZrO_2$ is within a range from 1/99–99/1, preferably 5/95–95/5 are preferred. Furthermore, in the present invention it is essential that the cerium and zirconium are forming a complex oxide. Use of a simple mixture of cerium oxide and zirconium oxide cannot achieve the objects of the present invention.

The component (B) is not limited to complex oxides of cerium and zirconium only, but it may contain the element(s) expressed by the symbol F in general formula (2) in the form of complex oxide. Typical methods for preparation of the component (B) include: (1) mix an aqueous solution of water-soluble cerium salt with that of water-soluble zirconium salt, dry and calcine the same; (2) react cerium oxide with zirconium oxide at solid phase; and (3) impregnate cerium oxide with aqueous solution of water-soluble zirconium salt, dry and calcine the same. The calcining temperature is normally 200–800° C., preferably 300–700° C. Upon such calcining, complex oxide containing cerium and zirconium is formed.

The ratio of component (B) to component (A) (as converted to oxides) is normally 0.5–30% by weight, preferably 1–20% by weight. When it is too low, the intended effect of adding component (B) cannot be attained, while if it is too high, yield drops as the production amount of the intended methacrylic acid reduces and those of $CO_2$ and CO increase.

The catalyst of the present invention can be used by itself or may be supported on inert carriers such as alumina, silica-alumina, silicon carbide, titanium dioxide, magnesium oxide, aluminium sponge and the like. In that occasion inorganic fibers such as glass fiber and various kinds of whiskers, which are generally well known for their effect of improving strength and attrition resistance of catalyst may be added. Also for controlling the catalyst properties with good reproducibility, additives generally known as powder binder such as ammonium nitrate, cellulose, starch, polyvinyl alcohol, stearic acid and the like may be used.

Shape of the catalyst is not critical, which may be any optional form such as pellets, spheres, columns, rings, tablets and the like. Their average diameter is 1–15 mm, preferably 3–10 mm.

Method for preparing the catalyst containing components (A) and (B) is subject to no critical limitation, and any optional method can be used. For example, advancedly prepared powders of the respective components are mixed, optionally using ball mill or the like to effect intimate mixing; or advancedly prepared component (B) is dispersed in component (A) under preparation, at an optional stage.

It is generally preferred for catalyst (I) to be used as molded catalyst as prepared by a process comprising thoroughly mixing the components (A) and (B); imparting to the mixture a desired shape, optionally adding water or the like as a molding aid; and calcining the same in an air stream at 300–600° C., preferably 350–500° C., for 1–10 hours, preferably 2–8 hours.

Catalyst (II) for producing methacrylic acid according to the present invention has the composition as expressed by the general formula (3) above, in which cerium and zirconium are forming a complex oxide. That is, catalyst (II) contains cerium and zirconium in the form of a complex oxide containing said two elements. A typical method for preparing this catalyst (II) is, similar to the one for preparing catalyst (I), to blend advancedly prepared components (A) and (B). Methods for preparing components (A) and (B), respectively, are same as already described.

Production of methacrylic acid according to the present invention can be carried out under the conditions normally employed in conventional methods for producing methacrylic acid from methacrolein, isobutylaldehyde, isobutyric acid or their mixtures, by vapor phase oxidation reaction and/or vapor phase oxidative dehydrogenation reaction, except that the catalyst of the present invention for producing methacrylic acid is used as the catalyst.

For example, a gaseous mixture comprising 1–10 vol. %, preferably 2–8 vol. % of at least one starting compound selected from the group consisting of methacrolein, isobutylaldehyde and isobutyric acid; 1–10 times by volume, preferably 1–8 times by volume, of the starting compound of molecular oxygen; and inert gas as a diluent, such as nitrogen, carbon dioxide, steam and the like (use of, in particular, steam is advantageous for improving the yield of the object product, because it inhibits formation of side products); is contacted with a catalyst of the present invention at temperatures ranging from 250 to 350° C., under pressures ranging from normal to 10 atmospheres, preferably from normal to 8 atmospheres, and at a space velocity ranging from 100 to 5,000 hr$^{-1}$ (STP), preferably from 500 to 4,000 hr$^{-1}$ (STP).

Where methacrolein is used as the starting compound, it is not necessary to use pure methacrolein and a methacrolein-containing gas obtained through catalytic oxidation of isobutylene, t-butanol or methyl-t-butylether can also be used. Use of such a methacrolein-containing gas is particularly recommendable in industrial processes.

The action of the component (B) in the methacrylic acid-producing catalyst of the present invention is presumed to be as follows: highly dispersible zirconium oxide inhibits aggregation of cerium oxide, to maintain the latter's promoting function to favorably absorb and release oxygen during the reaction, and whereby the oxidation reaction of methacrolein, isobutylaldehyde or isobutyric acid is accelerated, in consequence increasing the catalytic activity. Furthermore, degradation in the basic skeletal structure (Keggin structure) in the component (A) heteropolyacid due to its overreduction with time is inhibited (i.e., stability of the heteropolyacid is increased), resulting in extension of the catalyst life. Needless to say, the present invention however is not restricted by such theoretical observation.

EFFECT OF THE PRESENT INVENTION

Use of the catalyst of the present invention in vapor phase oxidation reaction and/or oxidative dehydrogenation reaction of at least one compound selected from the group consisting of methacrolein, isobutylaldehyde and isobutyric acid enables production of methacrylic acid at high yield. Because the catalyst of the present invention has a long life, it enables stable operation over prolonged period. Furthermore, the catalyst of the present invention enables stable operation over prolonged period also for heavy-load operation aiming at high productivity.

EXAMPLES

Hereinafter the present invention is explained more specifically, referring to working Examples, in which the conversion, selectivity and one-pass yield were calculated by the following equations.

Conversion (mol %)=(mol number of reacted starting compound/mol number of supplied starting compound)×100

Selectivity (mol %)=(mol number of formed methacrylic acid/mol number of reacted starting compound)×100

One-pass yield (mol %)=(mol number of formed methacrylic acid/mol number of suppled starting compound)×100

Example 1
<Catalyst preparation>

Into 7 liters of heated ion-exchange water, 1600 g of ammonium paramolybdate and 106.0 g of ammonium metavanadate were added and dissolved under stirring. Into this solution 104.5 g of ortho-phosphoric acid (85 wt %) and an aqueous solution formed by dissolving 206.1 g of cesium nitrate and 18.2 g of copper nitrate in 2 liters of ion-exchange water were added by the order stated, and the whole system was concentrated by heating under thorough stirring. Thus resulting slurry was dried at 250° C. for 16 hours and ground to provide a powder (powder A). Separately, 40.4 g of zirconium hydroxynitrate was completely dissolved in 1 liter of ion-exchange water, and into the solution aqueous ammonia was gradually added under stirring to precipitate hydrated zirconia sol. Then an aqueous solution of 262.3 g of cerium nitrate in 1 liter of ion-exchange water was added, and into the mixture of the solutions aqueous ammonia was further gradually added dropwise under stirring, until pH rose to 10. The resulting precipitate was filtered, washed with water, dried and calcined at 400° C. for 2 hours to provide a powder (powder B). Powder B was added to powder A and mixed well. Water was added to the mixture as a molding aid, and the mixture was molded into pellets of each 5.5 mm in outer diameter and 6.5 mm in length, which were dried and then calcined in a nitrogen stream at 400° C. for 3 hours and then in an air stream at 400° C. for 2 hours to provide catalyst (1). The elementary composition of this catalyst (1) was as follows, in terms of atomic ratio (excepting oxygen, as in all of the following Examples):

$Mo_{12}P_{1.2}V_{1.2}Ce_{0.8}Zr_{0.2}Cs_{1.4}Cu_{0.1}$.

It was confirmed by X-ray diffraction analysis that the cerium and zirconium in powder B were forming a complex oxide.

<Oxidation reaction>

A steel reactor of 25 mm in diameter was charged with 1200 ml of catalyst (1), and into which a gaseous mixture comprising 4 volume % of methacrolein, 9 volume % of oxygen and 20 volume % of steam, which was obtained by vapor phase oxidation of isobutylene in the presence of a molybdenum-bismuth-iron-cobalt polyelementary complex oxide catalyst, was introduced. The oxidation reaction of the methacrolein was conducted at 280° C. and space velocity of 1200 hr$^{-1}$ (STP). The result was as shown in Table 1.

Comparative Example 1

<Catalyst preparation>

Catalyst (2) was prepared in the same manner as in Example 1, except that powder B was not added.

<Oxidation reaction >

In Example 1, the oxidation reaction was conducted under identical conditions with those in Example 1, except that catalyst (2) was used in place of catalyst (1). The result was as shown in Table 1.

Example 2

According to Example 1, the oxidation reaction was continued for 8000 hours. The result after the 8000 hours' operation was as shown in Table 1.

As indicated in Table 1, the drop in conversion after 8000 hours' oxidation reaction was minor and there was almost no decrease in the yield. From this result it can be understood that the use of catalyst (1) enabled stable continuation of the oxidation reaction over a long period.

Comparative Example 2

According to Comparative Example 1, the oxidation reaction was continued for 8000 hours. The result after the 8000 hours' operation was as shown in Table 1.

Upon comparison of Example 2 with Comparative Example 2, it can be understood that the control catalyst (2) has a problem of short catalyst life, and when it is used in the reaction for many hours, decreases in conversion and yield are notable.

TABLE 1

|  | Catalyst No. | Reaction Temp. (° C.) | Methacrolein Conversion (mol %) | Methacrylic Acid Selectivity (mol %) | One-pass Yield of Methacrylic Acid (mol %) | Remarks |
|---|---|---|---|---|---|---|
| Example 1 | (1) | 280 | 84.5 | 80.8 | 68.3 |  |
| Comparative Example 1 | (2) | 280 | 80.6 | 80.7 | 65.2 |  |
| Example 2 | (1) | 280 | 81.8 | 81.0 | 66.3 | After 8000 hours |
| Comparative Example 2 | (2) | 280 | 72.0 | 80.7 | 58.1 | After 8000 hours |

Example 3

<Catalyst preparation >

Into 7 liters of heated ion-exchange water, 1600 g of ammonium paramolybdate and 97.2 g of ammonium metavanadate were added and dissolved under stirring. Into this solution 104.5 g of ortho-phosphoric acid (85 wt %) was added, followed by further addition of aqueous solution of 176.6 g of cesium nitrate and 18.2 g of copper nitrate in 2 liters of ion-exchange water, 22.7 g of 20 wt % silica sol and 11.0 g of antimony trioxide. The mixture was stirred thoroughly to provide a slurry (slurry A). Separately, 161.4 g of zirconium hydroxynitrate was completely dissolved in 1 liter of ion-exchange water, and into that solution aqueous ammonia was gradually added under stirring to precipitate hydrated zirconia sol, followed by addition of an aqueous solution of 65.6 g of cerium nitrate in 1 liter of ion-exchange water. Then aqueous ammonia was further slowly added to the mixture of the solutions dropwise under stirring until pH rose to 10. The resulting precipitate was filtered, washed with water, dried and calcined at 500° C. for 2 hours to provide a powder (powder B). Powder B was added to slurry A, and the mixture was concentrated by heating under stirring. The resulting slurry was dried at 230° C. for 15 hours and ground. Water was added to the resulting powder as a molding aid, and the mixture was molded into pellets of each 5.5 mm in outer diameter and 6.5 mm in length, which were dried and calcined in a nitrogen stream at 400° C. for 3 hours and then in an air stream at 400° C. for 2 hours to provide catalyst (3). The elementary composition of this catalyst (3) was as follows, in terms of atomic ratio: $Mo_{12}P_{1.2}Sb_{0.1}V_{1.1}Ce_{0.2}Zr_{0.8}Si_{0.1}Cs_{1.2}Cu_{0.1}$.

It was confirmed by X-ray diffraction analysis that the cerium and zirconium in powder B were forming a complex oxide.

<Oxidation reaction >

In Example 1, the oxidation reaction was conducted under identical conditions with those in Example 1, except that catalyst (3) was used in place of catalyst (1). The result was as shown in Table 2.

Comparative Example 3

<Catalyst preparation>

Catalyst (4) was prepared in the identical manner with the catalyst preparation in Example 3, except that the powder B was provided by mixing 74.4 g of a powder formed by 2 hours' calcining at 500° C. of the hydrated zirconia sol precipitate derived from zirconium hydroxynitrate, with 26.0 g of a commercial cerium oxide powder ($CeO_2$, specific surface area: 100 $m^2$).

<Oxidation reaction>

In Comparative Example 3, the oxidation reaction was conducted under identical conditions with those in Example 3, except that catalyst (4) was used in place of catalyst (3). The result was as shown in Table 2.

Upon comparing Example 3 with Comparative Example 3, it is understood that the catalyst (3) according to the invention excels in catalytic activity over the control catalyst (4).

Example 4

According to Example 3, the oxidation reaction was continued for 12000 hours. The result after the 12000 hours' operation was as shown in Table 2.

As indicated in Table 2, the drop in conversion after 12000 hours' oxidation reaction was minor and there was almost no decrease in the yield. From this result it can be understood that the use of catalyst (3) enabled stable continuation of the oxidation reaction over a long period.

Comparative Example 4

According to Comparative Example 3, the oxidation reaction was continued for 12000 hours. The result after the 12000 hours' operation was as shown in Table 2.

Upon comparison of Example 4 with Comparative Example 4, it can be understood that the control catalyst (4) has a problem of short catalyst life, and when it is used in the reaction for many hours, decreases in conversion and yield are notable.

Example 6

Example 3 was repeated except that the methacrolein content in the gaseous mixture fed into the reactor for the oxidation reaction was increased to 4.5 volume %. The result was as shown in Table 3.

Comparative Example 6

The oxidation reaction of Example 6 was repeated except that catalyst (3) was replaced with catalyst (4). The result was as shown in Table 3.

Upon comparing Example 6 with Comparative Example 6, it is understood that catalyst (3) of the present invention excels over the control catalyst (4) in both activity level and yield, also under high methacrolein concentration condition.

TABLE 3

| | Catalyst No. | Reaction Temp. (° C.) | Methacrolein Conversion (mol %) | Methacrylic Acid Selectivity (mol %) | One-pass Yield of Methacrylic Acid (mol %) |
|---|---|---|---|---|---|
| Example 5 | (3) | 290 | 84.7 | 81.2 | 68.8 |
| Comparative Example 5 | (4) | 290 | 80.3 | 81.1 | 65.1 |
| Example 6 | (3) | 280 | 84.6 | 80.1 | 67.8 |
| Comparative Example 6 | (4) | 280 | 80.4 | 80.0 | 64.3 |

Example 7

<Catalyst preparation>

Catalyst (5) was prepared in the identical manner with Example 3, except that the powder B was prepared with the amounts of the zirconium hydroxynitrate and cerium nitrate varied, yttrium oxide was added and the calcining was conducted at 650° C. for 1 hour. The elementary composition of this catalyst (5) was as follows, in terms of atomic ratio:

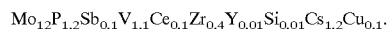

$Mo_{12}P_{1.2}Sb_{0.1}V_{1.1}Ce_{0.1}Zr_{0.4}Y_{0.01}Si_{0.01}Cs_{1.2}Cu_{0.1}$.

TABLE 2

| | Catalyst No. | Reaction Temp. (° C.) | Methacrolein Conversion (mol %) | Methacrylic Acid Selectivity (mol %) | One-pass Yield of Methacrylic Acid (mol %) | Remarks |
|---|---|---|---|---|---|---|
| Example 3 | (3) | 280 | 85.3 | 80.5 | 68.7 | |
| Comparative Example 3 | (4) | 280 | 81.1 | 80.3 | 65.1 | |
| Example 4 | (3) | 280 | 82.8 | 81.1 | 67.2 | After 12000 hours |
| Comparative Example 4 | (4) | 280 | 72.5 | 80.5 | 58.4 | After 12000 hours |

Example 5

Example 3 was repeated except that the oxidation reaction was carried out at 290° C. and at a space velocity of 1600 $hr^{-1}$ (STP). The result was as shown in Table 3.

Comparative Example 5

The oxidation reaction of Example 5 was repeated except that catalyst (4) was used in place of catalyst (3). The result was as shown in Table 3.

Upon comparing Example 5 with Comparative Example 5, it is understood that catalyst (3) of the present invention excels over the control catalyst (4) in the activity level and yield, also under high space velocity condition.

It was confirmed by X-ray diffraction analysis that the cerium, zirconium and yttrium were forming a complex oxide in Powder B.

<Oxidation reaction>

The oxidation reaction was conducted in the identical manner with Example 3, except that catalyst (5) was used in place of catalyst (3). The result was as shown in Table 4.

Examples 8–15

<Catalyst preparation>

Catalysts (6)–(13) were prepared in the identical manner with Example 7, except that the powder B was prepared with the amounts of the zirconium hydroxynitrate and cerium nitrate varied and that yttrium oxide was replaced with an oxide containing the element as indicated in Table 4 for each Example.

<Oxidation reaction>

The oxidation reaction of Example 7 was repeated except that catalyst (5) was replaced with catalysts (6)–(13) as indicated for each Example. The results were as shown in Table 4.

TABLE 4

| Catalyst Composition (atomic ratio excepting oxygen) $Mo_{12}P_{1.2}Sb_{0.1}V_{1.1}Si_{0.1}Cs_{1.2}Cu_{0.1}$ | | | Catalyst No. | Reaction Temp. (°C.) | Methacrolein Conversion (mol %) | Methacrylic Acid Selectivity (mol %) | One-pass Yield of Methacrylic Acid (mol %) |
|---|---|---|---|---|---|---|---|
| Ce | Zr | F | | | | | |
| Example 7 | 0.1 | 0.4 | Y = 0.01 | (5) | 280 | 85.3 | 80.3 | 68.5 |
| Example 8 | 0.1 | 0.5 | In = 0.02 | (6) | 280 | 84.8 | 80.4 | 68.2 |
| Example 9 | 0.4 | 0.6 | La = 0.02 | (7) | 280 | 84.7 | 80.7 | 68.4 |
| Example 10 | 0.4 | 0.6 | Pr = 0.015 | (8) | 280 | 84.1 | 80.9 | 68.0 |
| Example 11 | 0.6 | 0.4 | Sm = 0.01 | (9) | 280 | 83.8 | 80.8 | 67.7 |
| Example 12 | 0.2 | 0.8 | Co = 0.005 | (10) | 280 | 84.6 | 80.1 | 67.8 |
| Example 13 | 0.3 | 0.7 | Ni = 0.008 | (11) | 280 | 85.2 | 80.0 | 68.2 |
| Example 14 | 0.3 | 0.7 | Nd = 0.01 | (12) | 280 | 84.7 | 80.4 | 68.1 |
| Example 15 | 0.5 | 0.5 | Cu = 0.005 | (13) | 280 | 85.2 | 80.7 | 68.8 |

Example 16

Example 3 was repeated except that a gaseous mixture of 4.5 volume % of isobutylaldehyde, 11 volume % of oxygen, 10 volume % of steam and 74.5 volume % of nitrogen was used as the starting gas and that the space velocity was changed to 900 hr$^{-1}$ in the oxidation reaction. The result was as shown in Table 5.

Comparative Example 7

The oxidation reaction of Example 16 was repeated except that catalyst (3) was replaced with catalyst (4). The result was as shown in Table 5.

TABLE 5

| | Catalyst No. | Reaction Temp. (°C.) | Isobutylaldehyde Conversion (mol %) | Methacrolein Selectivity (mol %) | Methacrylic Acid Selectivity (mol %) | One-pass Yield of Methacrylic Acid (mol %) |
|---|---|---|---|---|---|---|
| Example 16 | (3) | 280 | 100 | 11.8 | 66.8 | 66.8 |
| Comparative Example 7 | (4) | 280 | 100 | 12.6 | 63.2 | 63.2 |

Example 17

Example 3 was repeated except that a gaseous mixture of 4.5 volume % of isobutyric acid, 10 volume % of oxygen, 10 volume % of steam and 75.5 volume % of nitrogen was used as the starting gas and that the space velocity was changed to 1800 hr$^{-1}$ in the oxidation reaction. The result was as shown in Table 6.

Comparative Example 8

The oxidation reaction of Example 17 was repeated except that catalyst (3) was replaced with catalyst (4). The result was as shown in Table 6.

TABLE 6

| | Catalyst No. | Reaction Temp. (°C.) | Isobutyric Acid Conversion (mol %) | Methacrylic Acid Selectivity (mol %) | One-pass Yield of Methacrylic Acid (mol %) |
|---|---|---|---|---|---|
| Example 17 | (3) | 280 | 99.0 | 78.8 | 78.0 |
| Comparative Example 8 | (4) | 280 | 96.5 | 77.9 | 75.2 |

What is claimed is:

1. A process for producing methacrylic acid through vapor phase catalytic oxidation, or vapor phase catalytic oxidation and catalytic oxidative dehydrogenation, or catalytic oxidative dehydrogenation of at least one compound selected from the group consisting of methacrolein, isobutylaldehyde and isobutyric acid with molecular oxygen or a molecular oxygen containing gas, the process being characterized in that it uses a catalyst characterized in that it is a complex oxide composition comprising (A) a complex oxide containing as essential components molybdenum and phosphorus, which is known per se as catalyst for said vapor phase catalytic oxidation and/or vapor phase oxidative dehydrogenation reaction expressed by the following general formula (1):

$$P_a Mo_b A_c B_d C_e D_f E_g O_x \qquad (1)$$

wherein P is phosphorus; Mo is molybdenum; A is at least one element selected from the group consisting of arsenic, antimony, germanium, bismuth and selenium; B is at least one element selected from the group consisting of copper, silver, iron, cobalt, nickel, lead, manganese, chromium, tin, zinc, palladium, rhodium and tellurium; C is at least one element selected from the group consisting of tungsten, vanadium and niobium; D is at least one element selected from the group consisting of alkali metals and alkaline earth metals; E is at least one element selected from the group consisting of titanium, silicon and aluminum; and O is oxygen; a,b,c,d,e,f g and x denote the atomic ratios of P, Mo, A, B, C, D, E and O respectively; and where b is 12, a is 0.5–4, c is 0.01–3, d is 0.01–5, e is 0.01–5, f is 0.01–6 and g is 0.01–10; and x is determined by the degree of oxidation of each of the elements and (B) a complex oxide containing cerium and zirconium as the essential components.

2. The process of claim 1 wherein component (B) of the catalyst is a complex oxide expressed by the following general formula (2):

$$Ce_1Zr_mF_nO_y \quad (2)$$

wherein Ce is a cerium; Zr is zirconium; F is at least one element selected from the group consisting of lanthanide series elements except cerium, yttrium, cobalt, nickel, copper, indium, tin, chromium and germanium; and O is oxygen; l, m, n and y denote the atomic ratios of Ce, Zr, F and O respectively, l and m being optional numbers not including 0, n being a number to satisfy the relationship $0 \leq n/(1+m) < 0.1$, and y being a number determined by the degree of oxidation of each of the elements.

3. The process of claim 1 characterized in that it uses a catalyst characterized by having a composition expressed by the following general formula (3):

$$P_aMo_bCe_cZr_dA_eB_fC_gD_hE_iG_jO_x \quad (3)$$

wherein P is phosphorus; Mo is molybdenum; Ce is cerium; Zr is zirconium; A is at least one element selected from the group consisting of arsenic, antimony, germanium, bismuth and selenium; B is at least one element selected from the group consisting of copper, silver, iron, cobalt, nickel, lead, manganese, chromium, tin, zinc palladium, rhodium and tellurium; C is at least one element selected from the group consisting of tungsten, vanadium and niobium; D is at least one element selected from the group consisting of alkali metals and alkaline earth metals; E is at least one element selected from the group consisting of titanium, silicon and aluminum; G is at least one element selected from the group consisting of lanthanide series elements except cerium, yttrium and indium; and O is oxygen; a,b,c,d,e,f,g,h,i,j and x denote the atomic ratios of P, Mo, Ce, Zr, A,B,C,D,E,G and O, respectively; and where b is 12, a is 0.5–4, c is 0.01–12, d is 0.01–16, e is 0.01–3, f is 0.01–5, g is 0.01–5, h is 0.01–6, i is 0.01–10 and j is 0.001–2, and x is numerical value determined by degree of oxidation of each the elements and the cerium and zirconium therein form a complex oxide.

* * * * *